(12) United States Patent
Enk

(10) Patent No.: US 10,118,007 B2
(45) Date of Patent: Nov. 6, 2018

(54) JET VENTILATION CATHETER, IN PARTICULAR FOR VENTILATING A PATIENT

(71) Applicant: DOLPHYS TECHNOLOGIES, B.V., Eindhoven (NL)

(72) Inventor: Dietmar Enk, Coesfeld (DE)

(73) Assignee: VENTINOVA TECHNOLOGIES B.V., Eindhoven (NL)

(*) Notice: Subject to any disclaimer, the term of this patent is extended or adjusted under 35 U.S.C. 154(b) by 502 days.

(21) Appl. No.: 14/744,009

(22) Filed: Jun. 18, 2015

(65) Prior Publication Data

US 2015/0283345 A1 Oct. 8, 2015

Related U.S. Application Data

(63) Continuation of application No. 12/561,196, filed on Sep. 16, 2009, which is a continuation-in-part of
(Continued)

(30) Foreign Application Priority Data

Mar. 16, 2007 (DE) .................. 10 2007 013 385
Mar. 17, 2009 (DE) .................. 10 2009 013 205

(51) Int. Cl.
*A61M 16/00* (2006.01)
*A61M 16/04* (2006.01)
(Continued)

(52) U.S. Cl.
CPC .... *A61M 16/0434* (2013.01); *A61M 16/0003* (2014.02); *A61M 16/0009* (2014.02);
(Continued)

(58) Field of Classification Search
CPC .......... A61M 16/0003; A61M 16/0009; A61M 16/0012; A61M 16/0096; A61M 16/04;
(Continued)

(56) References Cited

U.S. PATENT DOCUMENTS

| 3,581,742 A | 6/1971 | Glenn |
| 3,788,326 A | 1/1974 | Jacobs |

(Continued)

FOREIGN PATENT DOCUMENTS

| DE | 20213420 | 11/2002 |
| EP | 0 884 061 A2 | 12/1998 |

(Continued)

OTHER PUBLICATIONS https://courses.lumenlearning.com/ap2/chapter/gas-exchange/, Jan. 19, 2018.*
(Continued)

*Primary Examiner* — Bradley Philips
(74) *Attorney, Agent, or Firm* — Occhiuti & Rohlicek LLP

(57) ABSTRACT

The present invention relates to a catheter for ventilating a patient, with a ventilation channel for alternately delivering and removing air and/or oxygen to and from the patient's airways, the catheter having a maximum external diameter of at most 6 mm, preferably 2 to 5 mm, and the ventilation channel having an open end, and a connector end for connection to a gas flow reversing element. According to the invention, the catheter is provided with means or elements for measuring the pressure outside the ventilation channel near the open end. The catheter preferably has a pressure measurement channel, with an open measurement end near the open end of the ventilation channel, and a measurement connector piece for connecting a pressure display device. Of particular advantage is a catheter with an expansion body
(Continued)

(cuff) that is fluidically connected to a supply channel through which the expansion body can be increased or reduced in size by means of a fluid. The jet ventilation catheter according to the invention permits a novel ventilation principle that can be regarded as a bridge between classical jet ventilation and conventional controlled ventilation and that opens up possibilities for new and improved interventions in the airways.

15 Claims, 2 Drawing Sheets

Related U.S. Application Data application No. PCT/EP2008/053062, filed on Mar. 14, 2008.

(51) Int. Cl.
*A61M 16/20* (2006.01)
*A61M 16/08* (2006.01)

(52) U.S. Cl.
CPC .... *A61M 16/0012* (2014.02); *A61M 16/0096* (2013.01); *A61M 16/04* (2013.01); *A61M 16/0422* (2014.02); *A61M 16/0431* (2014.02); *A61M 16/0438* (2014.02); *A61M 16/0463* (2013.01); *A61M 16/0486* (2014.02); *A61M 16/0858* (2014.02); *A61M 16/20* (2013.01); *A61M 2016/0027* (2013.01); *A61M 2202/0208* (2013.01); *A61M 2205/02* (2013.01); *A61M 2205/3334* (2013.01); *A61M 2205/3348* (2013.01)

(58) Field of Classification Search
CPC .......... A61M 16/0422; A61M 16/0431; A61M 16/0434; A61M 16/0438; A61M 16/0463; A61M 16/0486; A61M 16/0858; A61M 16/20
See application file for complete search history.

(56) References Cited

U.S. PATENT DOCUMENTS

| | | | |
|---|---|---|---|
| 3,983,007 A | | 9/1976 | Au et al. |
| 4,405,314 A | | 9/1983 | Cope |
| 4,489,722 A | | 12/1984 | Ferraro et al. |
| 4,584,998 A | | 4/1986 | McGrail |
| 5,186,168 A | | 2/1993 | Spofford et al. |
| 5,188,604 A | | 2/1993 | Orth |
| 5,311,863 A | | 5/1994 | Toppses et al. |
| 5,447,152 A | * | 9/1995 | Kohsai ................. A61M 16/04 128/207.14 |
| 5,562,608 A | | 8/1996 | Sekins et al. |
| 5,669,380 A | | 9/1997 | Garry et al. |
| 5,791,341 A | * | 8/1998 | Bullard ................. A61M 16/04 128/207.15 |
| 5,906,204 A | | 5/1999 | Beran et al. |
| 5,915,383 A | | 6/1999 | Pagan |
| 5,954,636 A | | 9/1999 | Schwartz et al. |
| 6,287,290 B1 | | 9/2001 | Perkins et al. |
| 6,457,472 B1 | * | 10/2002 | Schwartz .......... A61M 16/0465 128/204.23 |
| 6,481,436 B1 | | 11/2002 | Neame |
| 6,874,504 B1 | | 4/2005 | Raspallo |
| 7,051,736 B2 | * | 5/2006 | Banner ................. A61M 16/04 128/204.21 |
| 7,588,033 B2 | * | 9/2009 | Wondka ............... A61M 16/04 128/200.26 |
| 2003/0228344 A1 | | 12/2003 | Fields et al. |
| 2004/0002725 A1 | | 1/2004 | Nicholson et al. |
| 2004/0154617 A1 | | 8/2004 | Enk |
| 2005/0005936 A1 | * | 1/2005 | Wondka ............... A61M 16/04 128/204.18 |
| 2007/0102000 A1 | | 5/2007 | Dhuper et al. |
| 2007/0277830 A1 | | 12/2007 | Ladru et al. |
| 2008/0142005 A1 | | 6/2008 | Schnell |
| 2008/0249503 A1 | | 10/2008 | Fields et al. |
| 2010/0236551 A1 | | 9/2010 | Enk |

FOREIGN PATENT DOCUMENTS

| | | |
|---|---|---|
| FR | 2287247 | 5/1976 |
| JP | 11-009694 | 1/1999 |
| JP | 2000308683 A | 11/2000 |
| JP | 2003503162 A | 1/2003 |
| JP | 2004283329 A | 10/2004 |
| JP | 2006181989 A | 7/2006 |
| JP | 2008523848 A | 7/2008 |
| JP | 2009508645 A | 3/2009 |
| WO | WO 99/66975 | 12/1999 |
| WO | WO 01/02042 A1 | 1/2001 |
| WO | WO 2006/055695 A1 | 5/2006 |
| WO | WO 2008/113752 | 9/2008 |

OTHER PUBLICATIONS

U.S. Appl. No. 12/561,196 entitled: Jet Ventilation Catheter, in Particular for Ventilating a Patient; Filed: Sep. 16, 2009.
Shenzhen Zhongyi Patent & Trademark Office. Chinese Office Action dated Jun. 5, 2014.Chinese Application No. 201080012329. X. Name of Applicant: Dolphys Technologies B.V.
Russian Office Action dated Apr. 25, 2014. Russian Patent Application No. 2011 141 706. Name of Applicant: Dolphys Technologies B.V. 11 pages.
Canadian Intellectual Property Office. Canadian Office Action dated Mar. 5, 2014. Canadian Application No. 2,678,892. Name of Applicant: Dolphys Technologies B.V. 5 pages.
Canadian Intellectual Property Office. Canadian Office Action dated Aug. 9, 2013. Canadian Application No. 2,678,892. Name of Applicant: Dolphys Technologies B.V. 4 pages.
Japanese Office Action dated Mar. 26, 2013. Japanese Application No. 2012-500234. 6 pages.
Japanese Office Action dated Dec. 24, 2013. Japanese Application No. 2012-500234. Name of Applicant: Dolphys Technologies B.V. English Translation. 4 pages.
Search Report for German Patent Application No. 10 2009 013 205.8 dated Jun. 15, 2010.
Comparison of four different emergency airway access equipment sets on a human patient simulator, Anaesthia, 2004, 59, pp. 73-79.
"A pressurized injection/suction system for ventilation in the presence of complete airway obstruction", Critical Care Medicine, vol. 22, No. 2, pp. 326-333.
International Search Report for PCT/EP2008/053062 dated Feb. 4, 2009.
International Preliminary Report on Patentability for PCT/EP2008/053062 dated Oct. 22, 2009.

* cited by examiner

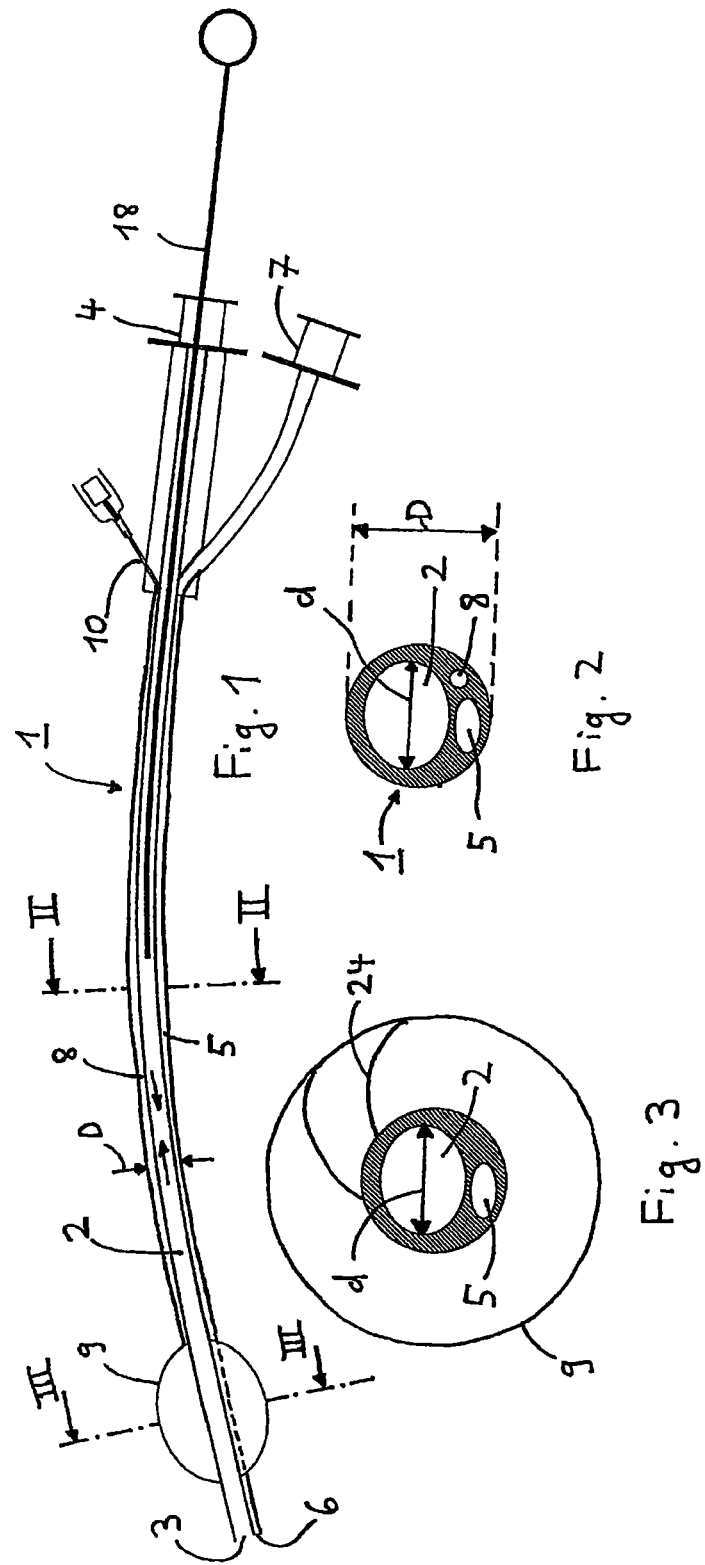

JET VENTILATION CATHETER, IN PARTICULAR FOR VENTILATING A PATIENT

CROSS-REFERENCES AND RELATED APPLICATIONS

This application is a continuation of U.S. application Ser. No. 12/561,196 entitled JET VENTILATION CATHETER, IN PARTICULAR FOR VENTILATING A PATIENT, filed on Sep. 16, 2009, which is a continuation-in-part of International Application No. PCT/EP2008/053062, filed on Mar. 14, 2008; the entire contents of which is hereby incorporated by reference and from which priority is claimed under 35 U.S.C. § 120. As in the parent application Ser. No. 12/561, 196, this application also claims the benefit of German Application No. DE 10 2007 013 385.7 filed on Mar. 16, 2007, and German Application No. 10 2009 013 205.8 filed on Mar. 17, 2009, the entire contents of which are also incorporated by reference and from which priority is claimed under 35 U.S.C. § 119.

FIELD OF THE INVENTION

The present invention concerns the ventilation of patients and their examination and treatment in the region of the airways.

BACKGROUND OF THE INVENTION

WO 2008/113752 A1 discloses a gas flow reversing element which allows a human being to be ventilated by way of a relatively thin catheter, for example in emergency situations. Oxygen can thus be introduced into the lung and gas can also be aspirated from the lung again in sufficient quantity. The high flow rate in both directions, despite the small diameter of the catheter, is able to maintain the supply of oxygen and the removal of carbon dioxide when ventilating through a relatively thin catheter.

Various devices for transtracheal ventilation are known from the article "Comparison of four different emergency airway access equipment sets on a human patient simulator" in Anaesthesia, 2004, 59, pages 73-79, in particular from FIG. 4, which shows an easy to use device for jet ventilation.

The main aim of the present invention is to extend the field of use of jet ventilation, to make it safer, and to create suitable devices and methods therefor. With classical jet ventilation, a mixture of oxygen and air is blown with a high pressure and flow via a katheter into the airway and used or excessive gas can escape via the airway. In contrast hereto, the concept of the present invention can be described as jet ventilation with expiratory assistance, which can also be used when this escape is not possible or is possible only with difficulty.

Surprisingly, the ventilation method hitherto conceived for emergency care in cases of partially or completely obstructed airways is also suitable for other uses. Hitherto, in operations performed in the region of the lower airways and the lungs, catheters with relatively large diameters have been used for ventilation purposes and for introducing instruments, but these restrict the possibilities of performing treatment alongside the catheter or of introducing additional catheters and instruments.

An additional and often underestimated problem is that, when a high concentration of oxygen is present in the airways and use is being made of a laser, for example, or of other instruments that generate high temperatures, there is a risk of burning. This concerns the surrounding tissue, but also the catheter and the instruments themselves.

An important aspect of jet ventilation is the safety of the patient during its use. In conventional jet ventilation systems, there is a danger that, if the airways are substantially or completely obstructed, too high a pressure will build up in the lung. Consequently, the field of use has hitherto been limited.

The object of the present invention is therefore to make available devices and methods which, in particular during an examination or operation, permit safe ventilation of a patient by means of jet ventilation with expiratory assistance and leave considerable parts of the cross-sectional area of the upper airways free for necessary interventions.

SUMMARY OF THE INVENTION

The foregoing object is achieved by a device and associated method according to the embodiments of the invention described herein.

In one embodiment, the present invention includes a catheter structured to be connected to a gas flow reversing element for ventilating a patient. According to one embodiment the catheter comprises an elongate member defining a ventilation channel therein for alternately delivering oxygen or oxygen containing gas to and removing respiratory gas from the patient's airways. The ventilation channel defines an open end and a connector end for connecting to the gas flow reversing element. Optionally, the catheter further comprises a pressure sensor located outside the ventilation channel for measuring the pressure near the open end of the ventilation channel.

In one embodiment, the elongate member has a maximum external diameter of approximately 6 mm. In another embodiment, the elongate member has an external diameter of approximately 1.5 to 4.5 mm. In yet another embodiment, at least a portion of the outer surface of the elongate member is made of a noncombustible, nonflammable and/or laser-resistant material and, preferably the outer surface of the elongate member insofar as it is to be inserted into the airways of a patient. In still another embodiment, at least a portion of the outer surface of the elongate member is coated with a noncombustible, nonflammable and/or laser-resistant material.

In one embodiment, the pressure sensor comprises at least one electronic pressure sensor with signal lines integrated within the elongate member of the catheter. In another embodiment, the elongate member further defines a pressure measurement channel therein, the pressure measurement channel defining an open measurement end near the open end of the ventilation channel and a second connector end. According to this embodiment, the pressure sensor comprises a measurement connector piece and a pressure display device, the measurement connector piece being operably connected to the second connector end and the pressure display device to measure the pressure within the pressure measurement channel.

In another embodiment, the elongate member, at least in the area of the open end of the elongate member, has a needle-like shape, being structured in particular for piercing the trachea and for performing transtracheal ventilation of a patient.

In another embodiment, the catheter comprises at least one expansion body positioned on the outside of the elongate member in the area of the open end of the elongate member, wherein the at least one expansion body is structured to be increased and reduced in size by delivering and removing a fluid, respectively. In one embodiment, the catheter comprises a supply channel defined within the elongate member or on the elongate member, the supply channel being fluidically connected to the expansion body. In yet another embodiment, the expansion body comprises at least one stabilizing structure that provides a minimum volume to the expansion body in the condition of reduced size and maintains at least the minimum volume of the expansion body relative to an external overpressure or underpressure of at least 10 mbar.

In one embodiment, the present invention includes a method for ventilating a patient, comprising the steps of providing a gas flow reversing element and providing a catheter comprising an elongate member defining a ventilation channel therein for alternately delivering oxygen or oxygen containing gas to and removing expiratory gas from the patient's airways, wherein the ventilation channel defines an open end and a connector end for connecting to the gas flow reversing element, the catheter further optionally comprising a pressure sensor located outside the ventilation channel for measuring the pressure near the open end of the ventilation channel. The method includes inserting the catheter from the outside into the trachea. Jet ventilation with expiratory assistance is performed through the catheter. In one embodiment, the performing step is conducted using a gas flow reversing element having processor-controlled valves for delivering and removing oxygen, oxygen containing gas and/or respiratory gas that is operably connected to the catheter. The pressure near the open end of the ventilation channel is measured; and the intervals for delivering and removing oxygen and/or air are determined based upon pressure measurement values.

In another embodiment, the catheter further comprises an expansion body and the method of the invention further comprises the step of intermittently modifying the size of the expansion body, the timing of the intermittent modifications in size being synchronized with the delivery and removal of air and/or oxygen in the performing step. In one embodiment, the step of intermittently modifying the size of the expansion body comprises increasing and reducing the size of the expansion body. In another embodiment, the step of intermittently increasing and decreasing the size of the expansion body comprises delivering and removing a noncombustible gas or a nonflammable liquid to the expansion body, respectively. In yet another embodiment, the noncombustible gas comprises nitrogen or a noble gas. And in yet another embodiment the nonflammable liquid comprises water or saline solution.

In one embodiment, the insertion step comprises inserting the catheter so far into the patient's airway that the expansion body is being positioned deeper than a site in the airway that is to be treated or examined, and the expansion body is at least intermittently expanded to such an extent that it holds the catheter sealingly in place relative to the surrounding tissue of the patient, and wherein the performing step is performed before, during and/or after the treatment of the site that is to be treated.

In one embodiment, the measuring step comprises measuring the pressure near the open end of the ventilation channel using an electrical pressure sensor positioned within the elongate member near the open end. In another embodiment, the elongate member further defines a pressure measurement channel therein, the pressure measurement channel defines an open measurement end near the open end of the ventilation channel and a second connector end, wherein the pressure sensor comprises a measurement connector piece and a pressure display device, the measurement connector piece being operably connected to the second connector end and the pressure display device, and wherein the measuring step comprises measuring the pressure near the open end of the ventilation channel using the pressure display device.

In still another embodiment, the present invention comprises a method of ameliorating a breathing obstruction in a subject, comprising the steps of providing a gas flow reversing element; providing a catheter comprising an elongate member defining a ventilation channel therein for alternately delivering and removing air and/or oxygen to and from the patient's airways, wherein the ventilation channel defines an open end and a connector end for connecting to the gas flow reversing element; inserting the catheter from the outside into the trachea; and performing jet ventilation with expiratory assistance through the catheter such that the subject is normoventilated. In one embodiment, the catheter further comprising a pressure sensor located outside the ventilation channel for measuring the pressure near the open end of the ventilation channel and the method further comprises the steps of measuring the pressure near the open end of the ventilation channel; and determining the intervals for delivering and removing oxygen and/or air based upon pressure measurement values. In another embodiment, the ventilation channel has a maximum diameter of 3 mm. In another embodiment, the flow rate of the inspirated and aspirated gas through the catheter is approximately 12 to 20 liters per minute. In still another embodiment, the flow rate of the inspirated and aspirated gas through the catheter is approximately 15 liters per minute.

BRIEF DESCRIPTION OF THE SEVERAL VIEWS OF THE DRAWINGS

Further details and advantages of the invention and preferred illustrative embodiments are explained in more detail below with reference to the drawings, in which:

FIG. 1 shows a catheter according to one embodiment of the invention for ventilation, particularly in examinations and operations;

FIG. 2 shows a cross section through the catheter according to FIG. 1 along the line II-II;

FIG. 3 shows a cross section through the catheter according to FIG. 1 along the line III-III;

DETAILED DESCRIPTION OF THE INVENTION

Figure 4:
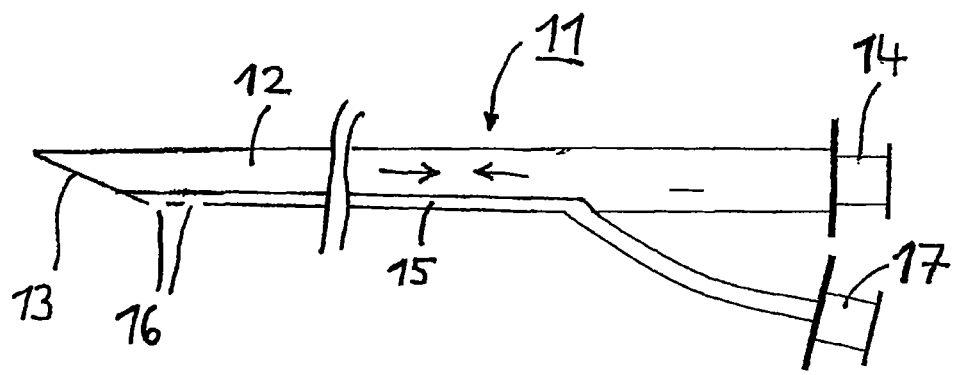
FIG. 4 shows a catheter according to another embodiment of the invention designed as a needle at the front for jet ventilation with expiratory assistance.

The detailed description begins with a general description of the invention and then concludes with a description of the embodiments of the invention illustrated in FIGS. 1-5.

For practically all uses of jet ventilation it is advantageous if a ventilation catheter introduced into the airways has, in the area of its open end, means or elements according to the invention for pressure measurement. Although this requires an additional channel or measurement conduits, this is offset by the gain in safety and by the possibilities of more precise dosing and control of the inhalatory and exhalatory gas flows. This broadens the possibilities of safe use of jet ventilation, particularly in connection with a gas flow reversing element, for example as described in WO 2008/113752 A1.

Although the measurement principle itself is not of importance, the measurement principle and the place of measurement should nevertheless be chosen in such a way that the actual ambient pressure near the open end of the catheter is measured, not the pressure in the interior of the channel for jet ventilation. Under these conditions, the jet ventilation according to the invention can even be used for transtracheal ventilation for example (i.e. via a cannula or needle (collectively refered to herein as a "cannula")) inserted through the skin into the trachea or via a catheter positioned in this way) if it is feared that the airways in the head-neck area are substantially or completely obstructed.

If the means or elements for pressure measurement include an additional channel, this can easily be kept open during introduction of the cannula or catheter, e.g. by an inner removable wire. Such a wire can also avoid buckling during the advance of the cannula or catheter.

In addition to a transtracheal cannula or transtracheal catheter intended particularly for emergency care and having means or elements for pressure measurement, the combination of the effect of a gas flow reversing element, for example as described in WO 2008/113752 A1, with a jet ventilation catheter according to the invention, as described below, defines a novel method of ventilation that can be regarded as a bridge between classical jet ventilation and conventional controlled ventilation and that opens up possibilities of new and improved interventions in the airways.

In an illustrative embodiment described in detail here and shown in the drawing, the special jet ventilation catheter is flexible, measures 20 to 60 cm in length, has an external diameter typically of at most 6 mm, preferably 1.5 to 4.5 mm, has a ventilation lumen measuring at most approximately 3 mm and with one or more openings at its ends, and, optionally, has a supply channel which leads to an expansion body located at the tip, here an inflatable cuff, and a pressure measurement channel, and it is preferably made from a noncombustible/nonflammable material or is coated with such a material. Resistance to laser radiation caused by lasers used in the medical field is also important in some applications, in order to ensure that the catheter cannot be damaged when such devices are used in its vicinity.

The tubular, flexible jet ventilation catheter is pushed through the mouth or nose into the trachea or, if it has a suitable length, as far as the bronchial system of the left or right lung of a patient. In contrast to the conventional bronchial blockers often used in unilateral surgery of the thorax, the jet ventilation catheter can be used to ventilate the "blocked lung", while at the same time the "unblocked lung" on the side to be operated on is able to collapse optimally (as is desired in such interventions).

Such a jet ventilation catheter can also be very easily positioned using a flexible fiber optic with a working channel. For this purpose, the tip of the jet ventilation catheter is fixed on the tip of the fiber optic by means of a filament or wire, which is guided through the catheter (for example through the pressure measurement lumen) and secured on the tip and which is then threaded back from the front end through the work channel of the fiber optic, and it is brought to the desired position with the fiber optic. The fiber optic is then pulled back. The filament or wire can be removed or left in place. The latter option allows the jet ventilation catheter to be repositioned at any time with the aid of the fiber optic.

The small external diameter ensures that the airway is only minimally obstructed by the jet ventilation catheter, such that plenty of room remains for diagnostic and therapeutic interventions, even in the deeper airways.

A ventilation lumen of less than 4.0 mm results in a considerably delayed passive exhalation. Consequently, adults can no longer be sufficiently ventilated by conventional means using such tubes. Because of the relatively high flow resistance of the ventilation lumen, e.g. with a diameter of 3 mm, the special jet ventilation catheter requires active support of exhalation by suction (e.g. by means of a gas flow reversing element) unless it is also possible (as in classical jet ventilation) for air to escape from the lung alongside the jet ventilation catheter.

By means of the inflatable cuff, the special jet ventilation catheter can seal off the trachea or a bronchus and thus separating the airways downstream and upstream of the expansion body.

Of particular advantage is a cylindrical cuff which (when inflated) holds the tip of the jet ventilation catheter in position in the middle of the trachea or of the bronchus and reduces the risk of dislocation during manipulations in the airway.

By means of the folds of the cuff material, even the "unblocked" cuff (that is to say emptied by suction) ensures that the opening(s) of the ventilation lumen are not sucked onto the wall of the trachea. However, it is also conceivable to use clasps (e.g. lying in the cuff) which hold the tip of the jet ventilation catheter in the lumen of the trachea or of a bronchus even when the cuff is completely empty.

The cuff can be inflated either continuously for the duration of an operation/intervention or intermittently at each ventilation cycle.

If the cuff is "blocked" continuously with a pressure of 20 to 30 mbar which is also customary in endotracheal tubes (in conventional controlled ventilation it is necessary to build up pressures of 20 to 30 mbar for sufficient gas exchange), the airway above the cuff is completely separated from the airway below the cuff (i.e. toward the lung periphery).

The airway above the cuff is then open to the outside, while the airway below the cuff by contrast is closed off from the outside. Thus, from classical jet ventilation (in what is generally an open airway), normoventilation—controlled ventilation with suction-assisted exhalation—is created, even in a blocked airway.

With the cuff blocked, the patient can even be given pure oxygen without increasing the oxygen-dependent risk of burns or flames which, in laser surgical interventions using electrocautery and in classical jet ventilation, necessarily arises with an increased oxygen concentration.

Alternatively, by intermittent inflation of the cuff during inhalation and emptying/collapsing of the cuff during exhalation, it is very easy, i.e. without needing to measure the intrapulmonary pressure, to avoid the build-up of too high a positive pressure or negative pressure in the lung.

Alternatively, it is also advantageous if the cuff is inflated and emptied again by suction automatically and in synchrony with the ventilation not via a separate channel, but instead via openings through which the cuff communicates with the ventilation lumen of the catheter. If the material of the cuff is elastic, the inflated cuff collapses still more quickly under the restoring forces of the cuff material.

Thus, during inhalation, it is possible to suppress the venturi effect, which characterizes jet ventilation and by which air is entrained from the upper airway into the lung and the inhalatory oxygen concentration is reduced, and it is possible to ensure a pressure compensation with the outside air upon each exhalation.

Moreover, by incomplete inflation of the cuff ("leaking" cuff) or inflation at a very low pressure (for example 5 mbar), it is possible to ensure that, in the presence of an overpressure or underpressure in the lung, the cuff becomes untight and then functions as an overpressure or underpressure valve.

The cuff and the sealing of the ventilated lung, which takes place at least during inhalation, also ensure that in laser surgical interventions with electrocautery, it is not possible for toxic fumes, virus particles or cell fragments, released by interventions above the cuff, to pass into the ventilated lung. Moreover, the ambient air in which the operating surgeon has to work is not additionally charged with the gas that flows out from the lung and that entrains such gases or particles.

By means of the cuff, it is very easy to switch from classical jet ventilation to jet ventilation with assisted expiration when so required, particularly during laser surgical interventions using electrocautery, and then to go back to classical ventilation again after the actual intervention and then allow the patient to wake.

After complete emptying of the cuff by suction, the jet ventilation catheter can then initially remain without any problem in the trachea of the wakened patient. It is then possible for oxygen to be administered through the jet ventilation catheter very effectively and without any danger and the patient in an emergency situation can even receive further (supportive) ventilation.

The jet ventilation catheter can also be used for renewed intubation or reintubation. For this purpose, the jet ventilation catheter simply has to be lengthened in a suitable way and can then serve as a guide for a conventional tube. Alternatively, a flexible wire is inserted through the lumen of the jet ventilation catheter into the deeper airways, the jet ventilation catheter is removed, and a suitable flexible rod (tube changer) is then engaged onto the flexible wire and positioned in the trachea, after which a conventional tube is advanced over this flexible rod into the trachea.

Although it is in principle possible to measure the intrapulmonary pressure through the ventilation lumen during a brief pause in ventilation, it is nevertheless desirable to provide an additional pressure measurement channel that permits continuous monitoring of the pressure. In tests, the lumen of an epidural catheter has already proven sufficient for this purpose. Although an air column in a channel with such a small lumen permits only a slightly delayed and attenuated measurement of the pressures during inhalation and exhalation, it nonetheless allows very simple and precise monitoring of the profile of the mean pressure (as the crucial parameter). In principle, it is of course also possible to carry out a precise measurement via a liquid column, by filling the pressure measurement channel with a sterile liquid and then connecting it to a transducer system. A miniaturized electronic pressure sensor can also conceivably be used and may be advantageous from the point of view of space requirements and production technology. However, an air or liquid column appears to be less susceptible to technical defects, and its functionality can be easily ensured and verified by flushing it through.

Pressure measurement in the ventilated lung then affords the possibility of controlling a ventilation device, for example based on the gas flow reversing element described in WO 2008/113752 A1 in such a way that the gas flows directed to and from the patient can be exactly adapted, in terms of their strength and duration, to the respective ventilation situation. In light of the increasing numbers of in particular laser surgical interventions with electrocautery in the region of the airways, the jet ventilation catheter should as far as possible be made of a noncombustible/nonflammable material. This is essential in particular in the case of ventilation with pure oxygen, since potentially life-threatening burns can otherwise occur in the airways of patients.

A catheter 1 according to the invention, and of a substantially tubular shape, is shown in FIG. 1. This catheter 1 has a maximum external diameter D of 6 mm, preferably of less than 4.5 mm. The catheter 1 does not necessarily need to have a circular cross section and instead can also have an oval cross section. Extending through the interior of the catheter 1 there is a ventilation channel 2, also called a lumen, for delivering oxygen or oxygen containing gas and removing respiratory gas. This ventilation channel 2, which also does not need to have a circular cross section, has a maximum internal diameter of up to 3 mm and affords the possibility of jet ventilation with expiratory assistance in which respiratory gas has to flow through the ventilation channel 2 in both directions. Accordingly, the structure of the catheter must be suitable to ensure that the cross-sectional area of the ventilation channel is maintained largely unchanged in the event of pressure and underpressure and in the event of bending. The ventilation channel 2 has an open end 3 through which respiratory gases can flow to and from the airways of a patient. The other end of the ventilation channel 2 is designed as a connector end 4 to which it is possible, in particular, to connect a gas flow reversing element 19 for delivering oxygen or oxygen containing gas and removing respiratory gas. Also extending through the catheter 1 is a pressure measurement channel 5, which has a measurement end 6 near the open end 3 of the ventilation channel 2, and which has a measurement connector piece 7 at the other end. The measurement end 6 can be arranged slightly offset in relation to the open end 3 of the ventilation channel 2. It is important on the whole that the measurement end 6 is designed and arranged in such a way that it cannot be closed off by tissue, secretions or the like during the aspiration of respiratory air through the ventilation channel 2. The outer surface of the catheter 1 is intended to be covered or coated with nonflammable material, unless it is possible for the entire catheter to be made of such a material. This reduces the risks of burning, particularly in an oxygen-rich environment. At a slight distance from the open end 3 of the ventilation channel 2, an expansion body 9, particularly in the form of a cuff, is arranged about the outer surface. A supply channel 8 leads to this expansion body 9, through which supply channel 8 it is possible to deliver fluid to and remove fluid from the expansion body 9. At its other end, this supply channel 8 terminates in a supply connector piece 10, which can be connected to customary devices that are known per se for operating such expansion bodies 9. In particular, the expansion body 9, the supply channel 8 and an associated operating element can be filled with a non-combustible and nonflammable fluid or gas, in particular nitrogen, a noble gas, water or saline solution. The expansion body 9 can be supplied by the supply channel 8 with so much fluid that it bears snugly on the walls around the site of its insertion, thereby holding the catheter 1 in position and substantially sealing off from each other the airways downstream and upstream of the expansion body 9. In its interior, the expansion body 9 can also have stabilizing structure 24 which, even without expansion by means of a fluid, maintain certain shapes or forces of the expansion body. The intention of the stabilizing structure (which may comprise, for example, straps, a sponge, a gel, etc.) that can be incorporated in the expansion body is to keep the expansion body's shape at least partially expanded if the expansion body is not inflated with gas or liquid.

To illustrate the size ratios, FIG. 2 shows a cross section through FIG. 1 along the line II-II, from which will be seen the arrangement of the ventilation channel 2 with an internal diameter d, of the pressure measurement channel 5 and of the supply channel 8 in relation to the external diameter D of the catheter. In this illustrative embodiment, the individual channels are formed separately from one another in one tube. However, it is also possible to arrange three separate tubes within a common sleeve or also to arrange the supply channel and pressure measurement channel as separate conduits within the ventilation channel.

FIG. 3 shows a cross section through FIG. 1 along the line III-III, that is to say in a plane through the expansion body 9. Since the supply channel 8 leads only as far as the start of the expansion body, this channel is no longer present in this cross section or, if present, has no function.

FIG. 4 shows a cannula according to the invention for jet ventilation with expiratory assistance. This cannula 11 is cannula-shaped in order to pierce into the trachea of a patient from the outside. A preferred embodiment consists of a cannula, within its interior or on its exterior a trocar designed for piercing into the trachea. For embodiments with the trocar positioned within the interior of the cannula, the trocar can be removed after the insertion and then the cannula is connected to a gas flow reversing element. The cannula 11 has a first ventilation cannula channel (lumen) 12 for delivering oxygen and removing respiratory gas, with an open end 13 and a connector end 14. Moreover, the cannula 11 has a pressure measurement channel 15 which extends alongside the first cannula channel 12 and which, near the cannula tip, has a measurement opening 16 and, at the other end, has a measurement connector piece 17. The connector end 14 of the first cannula channel 12 and the measurement connector piece 17 can be connected and used in the same way as in the catheter described in FIG. 1. As has been described, not only is oxygen injected into the lungs by jet ventilation with expiratory assistance, respiratory air is also aspirated in alternation with the delivery. Even in airways that are completely obstructed in the head-neck area, this permits the use of effective jet ventilation in the sense of transtracheal ventilation. To ensure that no excessive pressure is built up in the lungs despite the obstructed airways, an independent measurement channel in the cannula is particularly advantageous. Once again, the measurement opening 16 of the pressure measurement channel 15 of the cannula 11 should be arranged and designed such that, with a high degree of safety against blockage of the pressure measurement channel 15, an intermittent or as far as possible continuous measurement of the pressure in the trachea is possible. In another preferred embodiment the measurement channel 15 is separate from the cannula at the moment of piercing into the trachea and only after removal of the cannula is inserted via the measurement connector piece 7 inside and through the ventilation channel 12. Once again, the measurement opening 16 of the pressure measurement channel 15 of the cannula 11 should be arranged and designed such that, with a high degree of safety against blockage of the pressure measurement channel 15, an intermittent or as far as possible continuous measurement of the pressure in the trachea is possible.

Figure 5:
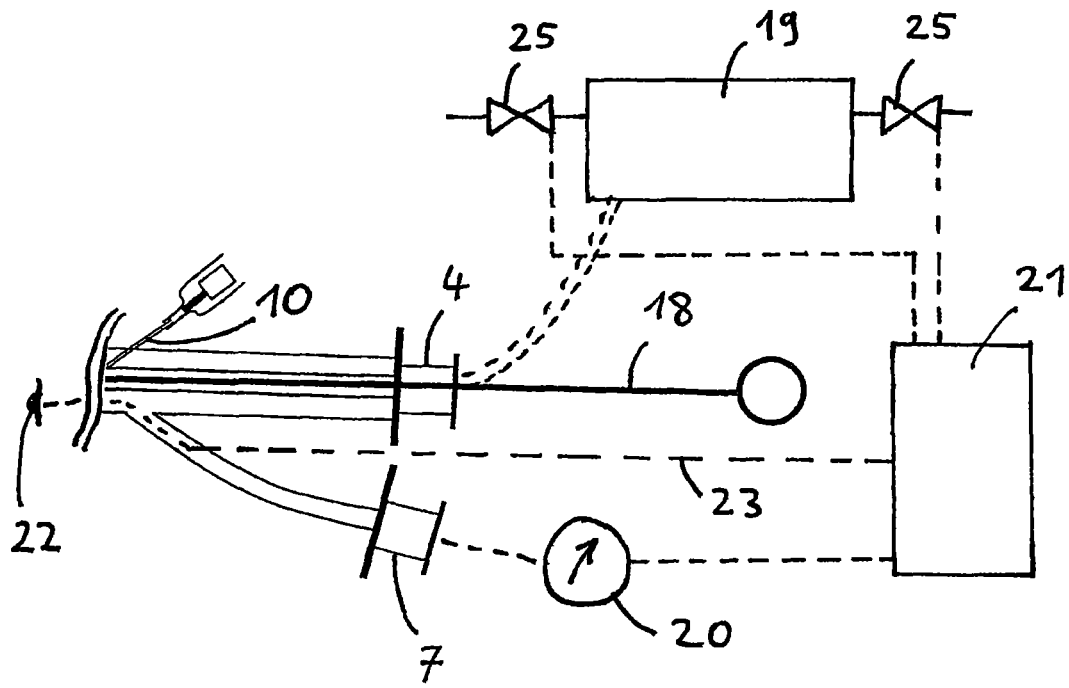
FIG. 5 shows an example of the arrangement of the catheter according to one embodiment of the invention with peripheral devices.

FIG. 5 shows a catheter 1 according to the invention with various peripheral devices. First, it is possible to insert a guide wire 18 into the ventilation channel 2 via the connector end 4 of the ventilation channel, in order to give the catheter 1 greater stiffness during positioning and to be able to move the open end 3 to a desired location in the airways of a patient. This guide wire 18 can also be used to push secretions or tissue out of the ventilation channel 2 in the case of blockage. After the guide wire 18 has been removed, the connector end 4 can be connected to a gas flow reversing element 19. In the simplest case, this gas flow reversing element can operate according to the principle described in WO 2008/113752. However, it is also possible to use an automated gas flow reversing element 19 in which valves 25 are controlled by a control processor 21 and ensure that oxygen or oxygen containing gas and respiratory gas is alternately delivered through the ventilation channel and removed from the ventilation channel.

Moreover, a pressure display device 20 is provided, to which the measurement connector piece 7 of the catheter 1 can be connected. Alternatively, FIG. 5 also indicates schematically that, instead of a pressure measurement channel 5, it is also possible for an electronic pressure sensor 22 to be integrated with signal lines 23 into the catheter 1, in particular for greater automation of the system. In this case, the sensor signals of the electronic pressure sensor 22 are fed to the control processor 21 for controlling the valves 25 in the gas flow reversing element 19.

The present invention enhances patient safety during jet ventilation with expiratory assistance and opens new areas of use of this method for ventilation via conduits of small cross section.

The catheter and/or cannula according to the present invention can advantageously be used to ventilate patients having an inadequate respiratory function on their own. In particular, the catheter and/or cannula according to the present invention can be used to ventilate patients with partially or fully obstructed, nearly complete or even completely blocked airways. With the catheter and/or needle according to the present invention it is possible to normoventilate these patients through a small lumen, in particular between 1.5 mm and 4.5 mm, preferably 3 mm or less, by jet ventilation with expiratory assistance.

Furthermore, it is advantageous to use a catheter and/or a cannula according to the present invention with an expansion body located at or near the tip of the catheter and/or cannula, which ensures in use inter alia a) that the usual airway is blocked (hereby smoke inhalation during laser resection and aspiration of blood, possibly carcinogenic or viral material or cell debris is avoided for the patient and environmental pollution with infection risk is excluded for medical personnel); b) that the position of the catheter and/or needle according to the present invention is fixed relative to the airway in lateral and/or radial position; c) that the tissue of the airway is not harmed or wounded by the catheter and/or needle. The expansion body comprises preferably an inflatable cuff. The expansion body is in use preferably expanded by insufflating an inert gas like in particular nitrogen or one or more noble gases or a non-flammable liquid in particular water or saline solution into the expansion body. The size and in particular at least one diameter of the expansion body can be controlled by the pressure of the gas or the liquid within the expansion body.

The method for jet ventilation of a patient with expiratory assistance can in particular be used in case of one of the following indications:

a) transtracheal jet ventilation;

b) ventilation via small lumen catheters in case of obstructed, nearly complete or even completely blocked airways due to pharyngeal, laryngeal, tracheal or bronchial tumor (e.g. carcinoma, submucosal edema, bleeding, emphysema);

c) one lung ventilation via small lumen catheters; and d) diagnostic and/or therapeutic intervention in the airway limiting the size of the artificial airway (e.g. endotracheal tube) that can be placed for maintaining adequate ventilation of a patient.

The method for jet ventilation of a patient with expiratory assistance can in particular be used in case of the following medical conditions:

a) pharyngeal, laryngeal, tracheal, bronchial airway obstruction limiting passive backflow from the lungs;

b) pharyngeal, laryngeal, tracheal, bronchial airway obstruction limiting the size of an artificial airway (e.g. endotracheal tube) that can be placed for maintaining adequate ventilation;

c) pharyngeal, laryngeal, tracheal, bronchial airway obstruction limiting the size of the artificial airway (e.g., endotracheal tube) that can be placed for maintaining adequate ventilation during diagnostic and/or therapeutic interventions in the airway;

d) "cannot ventilate, cannot intubate" situation; and e) support of cardiocirculatory resuscitation by alternately creating negative and positive intrathoracic pressure.

The term "normoventilation" is understood as (in combination with sufficient oxygenation) adequate removal of carbon dioxide accumulated by aerobic metabolism (with an alveolar ventilation rate that produces an alveolar carbon dioxide pressure of about 40 mm Hg at any metabolic rate).

The catheter and/or cannula according to the present invention is preferably made of a non combustible material or a material of low flammability and/or a material being resistant against laser beams, in particular of laser beams usually used in medical applications.

The ventilation method is preferably a manual ventilation method in which the flow of the respiratory gas to and from the patients airways are controlled manually, i. e. without the help of an automated gas flow reversing element. In this case the direction of the flow is controlled manually by an operator. Any type of gas flow reversing element can be used with the catheter and/or cannula according to the present invention. Preferred is the use of a gas flow reversing element according to WO 2008/113752 A2 which is incorporated herein by reference, in particular regarding the way the gas flow reversing element is formed or shaped.

Furthermore, a method for jet ventilation of a patient with expiratory assistance by means of a catheter and/or a needle according to the present invention is proposed in which the pressure of the respiratory gas in the airway and/or in the lung of the patient is controlled whereas the pressure is in particular used to control the volume flow of the respiratory gas to and from the airways of the patient.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other changes, combinations, omissions, modifications and substitutions, in addition to those set forth in the above paragraphs, are possible. Those skilled in the art will appreciate that various adaptations and modifications of the just described embodiments can be configured without departing from the scope and spirit of the invention. Therefore, it is to be understood that, within the scope of the appended claims, the invention may be practiced other than as specifically described herein.

What is claimed:

1. A method for ventilating a patient, comprising:
   providing a gas flow reversing element;
   providing a catheter comprising an elongate member defining a ventilation channel therein structured for alternately delivering oxygen or oxygen containing gas to and removing respiratory gas from the patient's airways, wherein the ventilation channel defines an open end and a connector end for connecting to the gas flow reversing element;
   wherein said elongate member is flexible, has an external diameter of no more than approximately 6 mm, wherein the catheter is structured to provide a flow rate of inspirated and aspirated gas of 12 liters per minute to 20 liters per minute, wherein the ventilation channel has a maximum diameter of 3 mm, and wherein the flow rate of the inspirated and aspirated gas through the catheter is 12 to 20 liters per minute;
   inserting the catheter from the outside into the trachea; and
   performing jet ventilation with expiratory assistance through the catheter.

2. A method according to claim 1, wherein said performing step is conducted using a gas flow reversing element having processor-controlled valves for alternately delivering oxygen or oxygen containing gas to and removing respiratory gas that is operably connected to the catheter.

3. A method according to claim 1, further comprising measuring the pressure near the open end of the ventilation channel; and
   determining intervals for delivering and removing oxygen and/or air based upon pressure measurement values to produce an alveolar carbon dioxide pressure of about 40 mm Hg.

4. A method according to claim 3, wherein the elongate member further defines a pressure measurement channel therein, the pressure measurement channel defines an open measurement end near the open end of the ventilation channel and a second connector end, wherein the pressure sensor comprises a measurement connector piece and a pressure display device, the measurement connector piece being operably connected to the second connector end and the pressure display device, and wherein said measuring step comprises measuring the pressure near the open end of the ventilation channel using the pressure display device.

5. A method according to claim 3, wherein said measuring step comprises measuring the pressure near the open end of the ventilation channel using an electrical pressure sensor positioned within the elongate member near the open end.

6. A method according to claim 1, the catheter further comprising at least one expansion body positioned on the outside of said elongate member in the area of said open end of said elongate member, wherein said at least one expansion body is structured to be increased and reduced in size by delivering and removing a fluid, respectively, and a supply channel defined within said elongate member, said supply channel being fluidically connected to said expansion body.

7. A method according to claim 6, further comprising the step of modifying the size of the expansion body until the expansion body seals off the airways.

8. A method according to claim 7, wherein the insertion step comprises inserting the catheter so far into the patient's airway that the expansion body is being located deeper than a site in the airway that is to be treated or examined, and the expansion body is at least intermittently expanded to such an extent that it holds the catheter sealingly in place relative to the surrounding tissue of the airway, and wherein said performing step is performed before, during and/or after the treatment of the site that is to be treated.

9. A method according to claim 6, further comprising the step of intermittently modifying the size of the expansion body, the timing of the intermittent modifications in size being synchronized with alternately delivering oxygen or oxygen containing gas to and removing respiratory gas in said performing step.

10. A method according to claim 9, wherein the step of intermittently modifying the size of the expansion body comprises increasing and reducing the size of the expansion body.

11. A method according to claim 10, wherein said step of intermittently increasing and decreasing the size of the expansion body comprises delivering and removing a non-combustible gas to the expansion body, respectively.

12. A method according to claim 11, wherein the non-combustible gas comprises nitrogen or a noble gas.

13. A method of ameliorating a breathing obstruction in a subject, comprising:
providing a gas flow reversing element;
providing a catheter comprising:
an elongate member defining a ventilation channel therein structured for alternately delivering and removing air and/or oxygen to and from the patient's airways, wherein the ventilation channel defines an open end and a connector end for connecting to the gas flow reversing element;
wherein said elongate member is flexible, has an external diameter of no more than approximately 6 mm so that said elongate member can be pushed through the mouth or nose into the trachea and as far as the bronchial system of the left or right lung of the patient, and so that the patient can be normoventilated via the catheter only, said elongate member structured to remove respiratory gas from the patient's airways at a rate sufficient to produce an alveolar carbon dioxide pressure of about 40 mm Hg, wherein the catheter is structured to provide a flow rate of inspirated and aspirated gas of 12 liters per minute to 20 liters per minute;
inserting the catheter from the outside into the trachea, wherein the ventilation channel has a maximum diameter of 3 mm, and wherein the flow rate of the inspirated and aspirated gas through the catheter is 12 to 20 liters per minute; and
performing jet ventilation with expiratory assistance through the catheter such that the subject is normoventilated at a rate sufficient to produce an alveolar carbon dioxide pressure of about 40 mm Hg.

14. A method according to claim 13 wherein the catheter further comprising a pressure sensor located outside the ventilation channel for measuring the pressure near the open end of the ventilation channel and the method further comprises:
measuring the pressure near the open end of the ventilation channel; and
determining the intervals for delivering and removing oxygen and/or air based upon pressure measurement values.

15. The method according to claim 13, wherein the flow rate of the inspirated and aspirated gas through the catheter is approximately 15 liters per minute.

* * * * *